(12) United States Patent
Baumann et al.

(10) Patent No.: US 6,475,760 B1
(45) Date of Patent: Nov. 5, 2002

(54) METHOD FOR INTRACELLULAR MANIPULATION OF A BIOLOGICAL CELL

(75) Inventors: Werner Baumann, Freiburg; Ralf Ehret, Merdingen; Mirko Lehmann, Freiburg; Günter Igel, Teningen; Hans-Jürgen Gahle, Emmendingen; Bernhard Wolf, Stegen; Ulrich Sieben, Reute; Ingo Freund, Vogtsburg-Oberrotweil; Martin Brischwein, Freiburg, all of (DE)

(73) Assignee: Micronas GmbH, Freiburg (DE)

( * ) Notice: Subject to any disclaimer, the term of this patent is extended or adjusted under 35 U.S.C. 154(b) by 0 days.

(21) Appl. No.: 09/321,051

(22) Filed: May 27, 1999

(30) Foreign Application Priority Data

May 27, 1998 (DE) .......................................... 198 23 655
Jun. 23, 1998 (DE) ...................................... 298 11 066 U
Sep. 10, 1998 (DE) .......................................... 198 41 337

(51) Int. Cl.⁷ .............................................. C12N 13/00
(52) U.S. Cl. ................................ 435/173.6; 435/173.4
(58) Field of Search ............................ 435/173.6, 173.4

(56) References Cited

U.S. PATENT DOCUMENTS 5,232,856 A * 8/1993 Firth
5,262,128 A  11/1993 Leighton et al.
5,457,041 A  10/1995 Ginaven et al.

FOREIGN PATENT DOCUMENTS

| DE | 40 31 138 A | 4/1991 |
|----|-------------|--------|
| DE | 40 04 198 A | 8/1991 |
| DE | 44 00 955 A | 6/1995 |
| EP | 0 292 899 A | 11/1988 |
| EP | 0 539 660 A | 5/1993 |
| WO | WO95/23211 | * 8/1995 |
| WO | WO 97/17426 A | 5/1997 |

OTHER PUBLICATIONS

Lundqvist et al., (1998) PNAS vol. 95, pp. 10356–10360.*
Teruel and Meyer, (1997) Biophys. J. vol. 73, pp. 1785–1786.*
Lundqvist et al., (1998) PITTCON '98, Poster Paper 1604P.*

* cited by examiner

*Primary Examiner*—Jon P. Weber
(74) *Attorney, Agent, or Firm*—Akin, Gump, Strauss, Hauer & Feld, L.L.P.

(57) ABSTRACT

A process is provided for the intracellular manipulation of a biological cell (3) which is positioned adhering to a support area (5) in a culture medium (2). Inside the support area (5) for the cell (3) an opening into the membrane of the cell (3) is created spaced from its support edge. The edge of the cell membrane surrounding the opening, adhering to the support area (5), thus seals off the cell fluid situated in the interior of the cell (3) from the culture medium (2) and insulates the cell fluid against the culture medium (2). The interior of the cell (3) is manipulated through the opening. An apparatus for implementing the process is also provided, including an object carrier (4) with a support area (5) for adhering the cell and a poration tool (6) for creating the opening in the cell membrane. The poration tool (6) may be any of various chemical, mechanical and/or electrical devices.

10 Claims, 4 Drawing Sheets

METHOD FOR INTRACELLULAR MANIPULATION OF A BIOLOGICAL CELL

BACKGROUND OF THE INVENTION

The invention concerns a method for intracellular manipulation of at least one deposited biological cell situated in a cultural medium adhering to a support area, wherein an opening is created in the membrane of the cell, and the cell interior is manipulated through this opening. The invention furthermore relates to an apparatus for manipulation of the cell interior of at least one biological cell having a cell membrane situated in a culture medium. The apparatus has an object carrier, which has at least one support area on which the cell is adherently depositable, a poration tool for opening the cell membrane, and at least one entry channel situated in the area of the poration tool for manipulation of the cell interior.

An apparatus of the type mentioned at the beginning is already known from Alberts, B. et al., *Molecular Biology of the Cell*, Third Printing, VCH Verlag (1995), page 212 ff, which has a hollow needle connected with a suction device and made of an electrical insulating material having an interior cavity which has an opening on the free end of the hollow needle. For opening the cell membrane, the opening situated at the free end of the hollow needle is set upon the exterior of the cell membrane in order then to create an underpressure in the interior cavity of the hollow needle by means of the suction device. Through this underpressure, a cell membrane piece situated in front of the opening of the hollow needle is torn out of the membrane formation. After introducing the opening into the cell membrane the hollow needle, engaging the edge of the cell membrane surrounding the opening, electrically insulates the cell fluid contained in the interior of the cell against the culture medium. The interior of the cell is manipulated through the opening introduced into the cell membrane. For example, the cell nucleus can be removed by sucking cell fluid into the hollow needle from the cell, and subsequently another cell nucleus can be installed through the opening into the cell interior.

The previously known process and the apparatus for implementing the process have the disadvantage that a micromanipulator is necessary for positioning the hollow needle on the cell. This results in a comparatively more complicated and expensive device. Moreover, the accessibility of the cells situated on the object carrier by the micromanipulator is greatly reduced. The process and the apparatus are, for this reason, only suited for an intracellular manipulation of individual, or at best for a simultaneous manipulation of a small number of cells situated on the object carrier. At the same time, a costly, manual positioning of the hollow needle on the cell is necessary.

Arranging a cell floating in a culture medium between two large surface area electrodes, respectively spaced at a distance from the cell, and applying an electric voltage to these electrodes is also already known from Alberts, B. et al., *Molecular Biology of the Cell*, Third printing, VCH Verlag (1995), page 213. Moreover, the membrane of the cell is simultaneously opened at several places by electroporation so that the genetic material situated in the culture medium to be introduced into the cell can be diffused into the cell interior through the openings of the cell. In this connection, however, it is disadvantageous that such an introduction of genetic material is subject to statistical fluctuations and is influenced by various parameters such as the concentration of genetic material in the area of the cell, the size of the genetic material to be introduced, and the size of the openings created in the cell membrane. The previously known process consequently does allow any selective manipulation of the cell interior.

SUMMARY OF THE INVENTION

There thus exists an object of creating a process and an apparatus of the type mentioned at the beginning, which make a simple manipulation of the interior of a cell possible. In particular, an expensive manual positioning of a hollow needle on the cell to be processed is to be avoided. This objective is accomplished according to the process of the invention in that the opening is introduced into the cell membrane within the support area of the cell and at a distance from its support edge.

In this manner, it is possible to arrange a poration agent for creating the cell membrane opening or a poration tool in the support area of the cell on the object carrier, so that when the cell is deposited on the support area, it is at the same time positioned on the poration agent or the poration tool. In this manner, an expensive manual positioning of a poration tool can be omitted. Since the opening is introduced into the cell membrane within the support area of the cell and at a distance from the edge of the support area, the membrane area of the cell surrounding the opening and adhering to the support area for the cell seals the opening against the culture medium. The cell fluid situated in the interior of the cell is thereby electrically insulated against the culture medium as extensively as possible, so that a potential equilization between the cell potential in the interior of the cell and that of the culture medium is prevented. Through the opening created into the cell membrane, the cell interior can be manipulated.

With an especially advantageous embodiment of the invention, the opening is introduced into the cell membrane by means of electroporation. While conducting the process, the electroporation electrode can, for example, be arranged in the support area on which the adhering cell lies. To introduce the opening into the cell membrane, only an electrical voltage then needs to be applied between the electroporation electrode and the culture medium. This brings about a flow of electrical current which opens the cell membrane.

With another embodiment of the invention, at least one mechanical impulse is exerted to introduce the opening into the cell membrane on a partial area of the cell membrane. In this connection, this partial area is released from the membrane formation. Optionally, an impulse succession can also be applied with several individual impulses.

It is especially advantageous if the opening is introduced into the cell membrane by means of sound waves, especially ultrasound and/or hypersound waves. Here, it is even possible for the sound waves to be focused on the area of the cell membrane to be opened and/or for several sound waves to be superimposed, such that their oscillations in the area of the cell membrane are overlaid into an oscillation with increased amplitude. The cell membrane can thereby be opened without contact.

A contact-free opening of the cell membrane can, however, also take place in that a partial area of the cell membrane is irradiated with energy-rich radiation, especially with laser radiation. In this connection, the wave length of the radiation is preferably selected such that the cell membrane absorbs the radiation well. Expediently, the radiation is launched into the cell at its support area. Optionally, however, a laser beam can also be launched into the cell outside the support area, in that first of all a small launch opening is introduced in a membrane area situated there. The laser beam is subsequently projected through the opening and through the interior of the cell to a membrane area situated in the support area of the cell, in order to cut out a partial area of the membrane from the membrane formation by swivelling the laser beam around the launch opening.

With another embodiment of the process, the opening is introduced into the cell membrane by the action of a chemical poration substance. Performing or Triton®, for example, can be used as poration agents.

It is especially advantageous if an electrical and/or chemical and/or a radiation-activatable chemical substance is used, and if this substance for introducing the opening into the cell membrane is activated by the action of radiation, a chemical and/or an electrical field. The substance is thus activated by supplying energy. In this manner, free radicals can be generated, for example, which destroy the partial area of the cell membrane to be opened. In the inactive state, the substance behaves largely neutrally toward the cell so that it practically does not influence placing the cell on the support area. A chemical substance which is activated by administering a further substance can also be used.

Another embodiment of the process provides that a partial area of the cell membrane to be opened is released from the membrane formation with an underpressure and/or an overpressure. For this purpose, for example, a small opening can be provided inside the support area on an object carrier having the support area. Suction is applied through the opening to the cell so strongly that the membrane area situated in front of the opening is torn out of the membrane formation. For opening the cell membrane, an overpressure impulse can also be exerted through the opening on a membrane area of the cell. It is advantageous for the cell to be fixed on the support area by the force of suction. In this manner the adhesion of the cell to the support area of the object carrier can be improved. The force of suction is here so proportioned that the cell membrane is not mechanically damaged by the force of the suction.

It is advantageous if after introducing the opening into the cell membrane at least one substance and/or one cell component is removed from the cell interior and/or placed in the cell interior though the opening. Thus, for example, a medication, a protein and/or another biologically active substance can be brought through the opening into the interior of the cell in order to test its reaction. However, a gene or gene fragment can also be removed from the cell or introduced into it. Even the cell nucleus can be removed from the cell through the opening and replaced by another.

With regard to the apparatus of the invention, the accomplishment of the object mentioned above consists in that the poration tool is arranged within the support area. The cell can thereby be deposited on the poration tool situated in the support area. Advantageously, an expensive manual positioning of the poration tool on the cell is thereby avoided. Furthermore, no auxiliary devices, for example micromanipulators, are needed. It is thus possible to manipulate intracellularly several cells arranged tightly adjacent to one another in the support area at the same time. After introducing the opening into the cell membrane, the edge of the cell membrane surrounding the opening remains in contact with the support area of the object carrier and seals the opening of the cell membrane against the culture medium An especially advantageous embodiment of the invention provides that the poration tool is bounded by at least one electrical insulator within the support area. By means of the electrical insulator, the cell fluid situated in the interior of the cell is then well insulated against the culture medium so that the interior of the living cell can be manipulated over a longer period of time without the cell dying off. The insulation resistance is dependent upon the cell type and is preferably greater than 10 megaohm. A potential equalization between the culture medium and the cell fluid is thereby prevented to the greatest extent. Optionally, the object carrier can consist wholly of an insulating material. The insulator can also, however, be arranged in the interior of the object carrier at a distance from the surface of the support area.

It is advantageous if the poration tool substantially concentrically surrounds the opening of the passage channel situated in the support area of the object carrier. The cell interior can then be even better manipulated through the opening without the edge area of the cell membrane surrounding the opening being damaged by the manipulation.

It is especially advantageous if the poration tool is an electroporation electrode, to which a reference electrode capable of being brought into contact with the culture medium is allocated, and if the electroporation electrode and the reference electrode are connectable for electroporation of the cell membrane with a source of electrical voltage. The electroporation electrode is arranged within the support area of the object carrier so that a cell adherently deposited on the insulator can likewise be deposited on the electrode, or at least can approach this up to the radius of action of an electrical field emanating from the electrode. When electroporation voltage is applied to the electrode, an electric current flows which introduces an opening into the cell membrane. At the same time, the edge of the cell membrane surrounding the opening remains in contact with the support area and seals off the opening against the culture medium. After creating the opening into the cell membrane, the electrode is separated from the electroporation voltage source, so that the interior of the cell can then be altered through the opening.

With one advantageous embodiment of the apparatus, the poration tool for opening the cell membrane is movable by means of an actuator, especially a piezo element, transversely to the surface of the support area relative to the object carrier. With this device, the opening is thus mechanically introduced into the cell membrane. The poration tool can thus be alternatively moved toward and away from the opening on the cell membrane. For this purpose, the actuator is connected with an activation facility for generating a mechanical vibration, especially an ultrasound or hypersound vibration. The poration tool can be mobile in a direction running at right angles or obliquely to the surface of the support area relative to the object carrier.

It is advantageous if the poration tool has at least one sharp tip or edge, preferably protruding relative to the surface plane of the support area. The poration tool can then optionally lie on the cell membrane, so that this can be mechanically opened even better. If the poration tool is an electrode for electroporation of the cell membrane, there results an especially high electric field strength when a poration voltage is applied to the electrode, which facilitates opening the cell membrane.

It is especially advantageous if a laser beam is provided as poration tool, and if the radiation path of the laser beam is passed through the entry channel to the opening situated in the support area. With this device, a partial area of the cell membrane can be irradiated for a short time with energy-rich optical radiation, wherein the latter is so strongly heated that the cell membrane opens. Optionally, beam guidance means can be arranged inside or outside the entry channel.

It is especially advantageous if a laser diode is incorporated into the object carrier for generating the laser beam. In this manner, the laser diode can even be arranged directly behind the opening of the entry channel so that the laser radiation can be launched directly and consequently largely free of loss into the cell membrane of the cell deposited on the support area.

It is provided with an advantageous embodiment of the invention that the poration tool for opening the cell membrane has a chemical poration substance in the support area of the object carrier and/or that a chemical poration substance can be fed in through the entry channel to its opening. The opening can thus also be introduced chemically into the cell membrane, whereby Performing or Triton® can be used as poration agents. Optionally, the entry channel can be connected or connectable with a deposit containing the poration substance, from which the poration substance is feedable to the cell membrane.

With another embodiment, the device has at least one pump which, for opening the cell membrane by contacting with underpressure or overpressure, is connected with the entry channel and/or the entry channel is connectable with an underpressure or overpressure reservoir through a valve or similar shut-off element. The opening can be introduced into the cell membrane through underpressure or overpressure, wherein the underpressure or overpressure is shut off following opening the cell membrane. In this manner, sucking off cell fluid from the interior of the cell during opening the cell membrane through underpressure is avoided to the greatest extent. Correspondingly, when opening the cell membrane using overpressure, any medium situated in the entry channel (which is preferably a fluid) can be prevented from reaching into the interior cell. For turning off the underpressure or overpressure, a pressure change occurring in the entry channel when opening the cell membrane can be determined. Advantageously, the entry channel can be also used before depositing the cell, in order to suck off culture medium from the support area, so that a current arises in the culture medium which leads the cells situated therein to the opening of the entry channel arranged in the area of the poration tool.

An advantageous embodiment provides that the poration tool is arranged on a projection protruding in relation to the surface plane of the support area. In this manner, there results a good electrical and/or mechanical contact between the poration tool and the cell membrane.

Expediently, it is provided that the cross section of the projection tapers at the furthest projecting point. The cell then adheres especially well on the support area of the object carrier in the area of the projection. Moreover, in terms of production engineering the insulator can be better applied during production of the object carrier as a coating to the tapering area of the projection.

With an advantageous refinement of the invention, it is provided that the object carrier has a contour in the support area, which has at least one profile depression running around the poration tool and/or one profile projection running around the poration tool. In this manner, a better sealing of the cell fluid against the culture medium by the cell membrane adhering to the insulator is obtained.

It is advantageous if the profile depression and/or the profile projection is interrupted by at least one gap in the projection direction. The cell can then adhere better in the area of the contouring to the surface of the object carrier. The profile projection or the profile depression can, for example, have a honeycomb structure, or a structure in the manner of a checker or chess board pattern.

It is especially advantageous if the profile depression and/or profile projection is constructed as a ring-shape, and if preferably several such annular profile depressions and/or profile projections are arranged substantially concentrically to the poration tool. Consequently, several profile depressions and projections are connected or inserted one after the other radially to the poration tool, so that the cell fluid is even better sealed off against the culture medium.

A preferred embodiment of the invention provides that the electrical insulator is an insulation layer arranged on the surface of the contour. Advantageously, with the insulation layer contoured in this manner, the path for a creeping current flowing on the surface of the insulator from the cell fluid to the culture medium is enlarged, so that the cell fluid situated in the interior of the cell is even better insulated against the culture medium after opening the cell membrane.

Another embodiment provides that the profile projection(s) is (are) installed on the surface of the electrical insulator. The object carrier is then easier to manufacture in terms of assembly.

It is especially advantageous if a cell coating having at least one cell adhesion protein and/or a hydrophilic coating and/or immediately adjacent to the poration tool a hydrophobic coating is arranged in the support area of the object carrier. The cell membrane then adheres better to the object carrier. The cell adhesion coating can include, for example, laminin, fibronectin or poly-L-lysine. Optionally, a hydrophobic coating with binding sites for hydrophobic lipids found in the cell membrane can also be arranged on the edge of the support area bordering on the electrode.

It is advantageous if, as a mechanical guide for the cells, boundary walls are arranged on both sides of the poration tool, which preferably delimit a groove-like guide channel. Moreover, the poration tool is preferably arranged in the middle between the boundary walls at the bottom of the groove of the guide channel, so that cells situated in the guide channel can essentially move only in the direction of extension of the guide channel and then necessarily come into contact with the poration tool.

It is advantageous if, for creating an electrical field leading the cell to the poration tool, at least one supplemental electrode is arranged in the support area and/or adjacent thereto. In this manner, an electric field can be created on the surface of the object carrier, which exerts a force on the biological cells, their dielectricity constants differing from those of the culture medium in which they are arranged, which leads the cells to the poration tool.

With a preferred embodiment of the invention, the object carrier is constructed approximately as a plate-shaped carrier element which has the support area on a flat side. The entry channel penetrates the object carrier proceeding from the support area to the reverse side of the object carrier facing away therefrom, and the object carrier has a wall weakening or thinning (attenuation) in the area of the entry channel, which in the direction of extension of the entry channel has a smaller dimension than a wall area adjacent to the wall attenuation. The entry channel is thus passed through the object carrier in the area of the wall attenuation and penetrates this, preferably at right angles to the plane stretching across the support area. In this manner, an especially short entry channel is obtained. The entry channel can, for example, be connected with a pump or a suction facility arranged on the reverse side of the object carrier. The wall area of the object carrier bordering on the wall attenuation, and preferably encircling it, has a greater wall thickness than the wall attenuation which improves the mechanical stability of the object carrier.

It is advantageous if the wall attenuation is arranged on a preferably funnel-shaped form formation in situated on the reverse side of the object carrier facing away from the support area. The support area can then be arranged in a plane extending up to and over the wall attenuation, so that the cells can better accumulate thereon.

An especially advantageous refinement of the invention provides that, in the support area, several poration tools having at least one entry channel are preferably arranged as arrays. With such a device, a plurality of cells closely adjacent to one another can be intracellularly manipulated, either at the same time or successively, whereby statistical fluctuations can be eliminated. Optionally, a multiplexer can be incorporated into the object carrier with which a plurality of electroporation electrodes can be controlled alteratively one after the other, whereby the number of supply leads to the object carrier is correspondingly reduced.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiment(s) which are presently preferred. It should be understood, however, that the invention is not limited to the precise arrangements and instrumentalities shown. In the drawings.

DETAILED DESCRIPTION OF THE INVENTION

Figure 1:
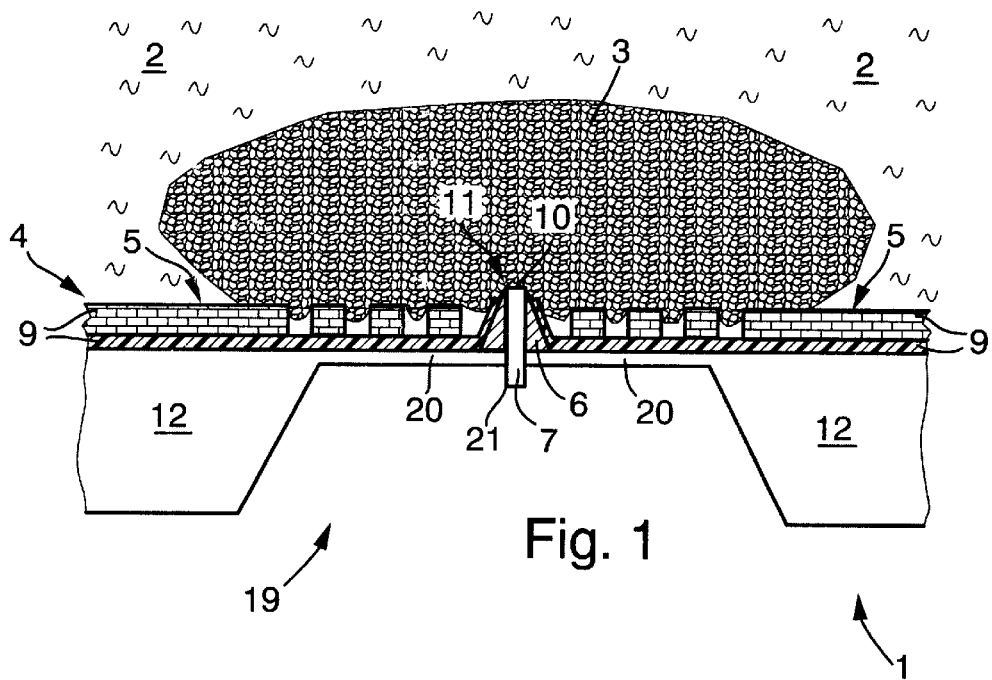
FIG. 1 is a longitudinal section through an apparatus of the invention for manipulation of the interior of a cell, having an object carrier with a poration tool, on which carrier a biological cell situated in a culture medium is adherently deposited.

An apparatus, designated overall with 1, for manipulation of the interior of a biological cell 3 situated in a culture medium 2 (FIG. 1) has an object carrier 4 which has a support area 5 on which the cell 3 can be adherently deposited. The cell 3 is thus immobilized on the object carrier 4 and adheres to the support area 5. For creating an opening into the cell 3 adhering to the support area 5, a poration tool 6 is arranged inside the support area 5. The object carrier 4 has a entry channel 7 for manipulation of the cell interior which opens into the support area 5 in the area of the poration tool 6. In the operating position, the edge of the support area 4 encircling the opening is arranged at a distance from the support edge of the cell 3. The membrane of the cell 3 adhering to the object carrier 4 thus encircles the opening of the entry channel 7, through which the cell fluid situated in the cell interior is sealed off against the culture medium 2 after creating the opening into the cell membrane.

Figure 2:
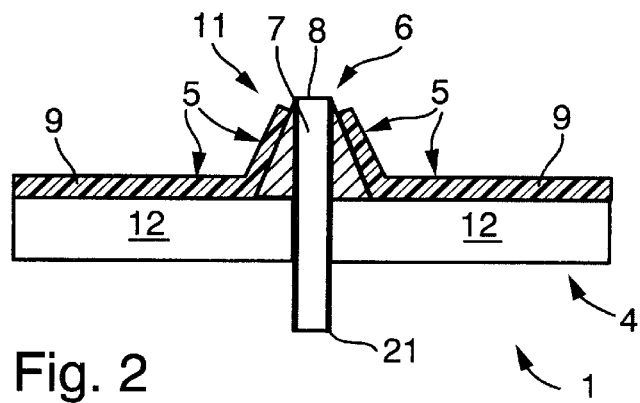
FIG. 2 is a longitudinal section through an apparatus similar to FIG. 1 wherein, however, the support area of the object carrier is uncontoured.
Figure 3:
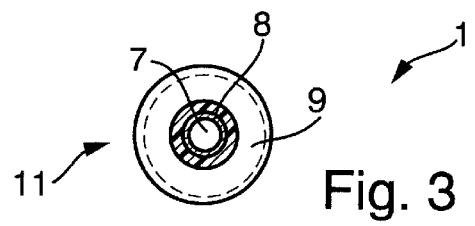
FIG. 3 is a plan view of the poration tool shown in FIG. 2.

With the embodiments according to FIGS. 1 to 3, the poration tool 6 is an electroporation electrode which has an active electrode area 8 projecting in relation to the surface plane of the support area 5. The electrode is constructed as a hollow electrode which is penetrated by the entry channel 7. A segment of the entry channel 7 extends from the end of the electrode facing away from the active electrode area 8 to the active electrode end 8. As is especially well recognizable in FIGS. 3 and 5, the active electrode area 8 encircles annularly the opening of the entry channel 7. Furthermore, an electrical insulator 9 surrounds the active electrode area 8 in the support area 5 on which the cell 3 is depositable sealed off against the culture medium 2.

The electrode is connected by means of a conductor path incorporated into the object carrier to an electric or electronic circuit element with which it is connectable with an electroporation voltage element. For opening the cell membrane, an electrical voltage is applied between the poration tool 6 and the culture medium 2, whereupon an electrical current flows into the cell membrane through the poration tool 6, which opens the cell membrane in the area of the poration tool 6. The opening introduced into the cell 3 by means of the poration tool 6 is sealed off against the culture medium 2 by the cell membrane area adhering to the insulator 9 of the object carrier 4. In this manner, a potential equalization between the potential of the cell fluid situated in the interior of the cell 3 and that of the culture medium 2 is prevented.

After opening the cell membrane, the interior of the cell 3 is manipulated through the entry channel 7. Here, for example, a substance can be removed from the cell interior and/or introduced into the cell interior through the entry channel 7. The substance can be, for example, a cell component, a gene, a protein, a toxic substance which the cell should detect, and/or a medication whose action on the cell should be examined, or with which the cell should be treated. Substances present in the cell or cell components can also be altered, in that they are, for example, irradiated through the entry channel 7 with energy-rich radiation. A micromanipulator or similar tool can also be introduced into the cell interior through the entry channel 7 to manipulate the cell interior there mechanically. In this manner, a change can be undertaken selectively at a certain place in the cell interior.

In the embodiments according to FIGS. 1 and 3, the poration tool 6 constructed as an electrode assumes approximately the shape of a conic section, wherein the substantially cylindrical entry channel 7 penetrates along the central axis of the cone. The symmetry axis of the electrode is at all times approximately at right angles to the surface plane of the object carrier 4 in the support area 5. The poration tool 6 can be wholly or partially sunk into the surface of the object carrier 4.

The active electrode region 8 of the electrode respectively surrounds the opening of the entry channel 7 and has a sharp ring edge projecting in relation to the surface plane of the support area 5, the cross section of which tapers proceeding from the surface plane of the object carrier to the furthest projecting point of the electrode. In this manner, an especially high electrical field intensity arises when an electroporation voltage is applied to the poration tool 6 in the active electrode region 8, which facilitates opening the cell membrane.

The portion of the entry channel 7 which penetrates the hollow electrode can be filled with culture medium 2. In this manner, the electric charge carrier can reach from the inner wall of the electrode surrounding the entry channel 7 to the cell membrane situated on the opening of the entry channel 7, whereby a greater active electrode surface results overall, and the electrical contact resistance between the electrode and the cell fluid is correspondingly diminished. The electrode surface can have a surface roughness which enlarges the surface of the electrode. The electrode can, for example, be made of porous silicon or have a coating of this or another porous material.

As is especially well recognizable in FIGS. 1, 4, 6 and 7, the electrical insulator 9 has a projection 11 inside the support area 5 protruding in relation to its surface plane, on whose free end facing away from the surface plane the active electrode area 8 of the electroporation electrode is arranged. The active electrode area 8 is thereby electrically well-connected to the cell 3 adhering to the support area. The cross section of the projection 11 tapers proceeding from the surface plane of the support area 5 to the furthest protruding point. In this manner, the projection 11 and the electrode can be better produced in terms of manufacturing technology. Moreover, the tapering projection 11 makes possible a good mechanical stability. The projection 11 can, however, also have a constant cross section in the direction of its extension. The projection 11 can, for example, also be manufactured using LIGA technology.

The object carrier 4 has a subatantially plate-shaped substrate 12 which, for example, can be made of a semiconductor material (for example silicon or gallium arsenide), silicon carbide, glass or plastic. On this substrate, the insulator 9 can be applied as a coating, for example by sputtering. Optionally, the substrate 12 can also be a flexible sheet.

Figure 6:
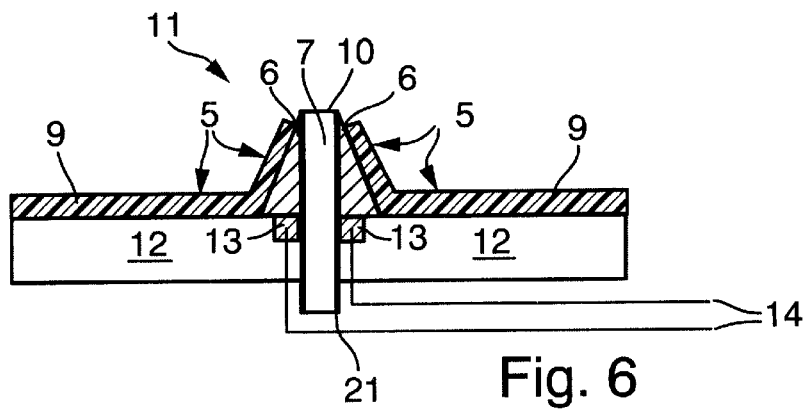
FIG. 6 is a longitudinal section through an apparatus in which the poration tool is movable by means of a piezo element.

In the embodiment according to FIG. 6, a piezo element 13 is arranged between the poration tool 6 and the substrate 12 of the object carrier 4, which bears the poration tool 6 on its free end movable relative to the object carrier 4. This has a sharp ring edge 10 on its end facing away from the piezo element 13, which engages the cell 3 in the operating position. With its end facing away from the poration tool 6, the piezo element 13 is fixed on the substrate 12 of the object carrier 4. In the support area 5, the insulator 9 enclosing the poration tool 6 is arranged, which is led over the cone casing surface of the poration tool 6 up to right on its sharp edge 10. By means of the piezo element 13, the edge 10 of the poration tool 6 can be moved relative to the object carrier 4 toward or away from a cell 3 positioned on the support area 5, approximately in a direction normal to the plane stretching across the support area 5 . For thiws purpose, the piezo element 13 is connectable by means of electrical connections 14 with a current supply. The insulator 9 consists of an elastic material which makes possible a relative motion between the poration tool 6 and the substrate 12 of the object carrier 4 during activation of the piezo element by the connections 14.

With the piezo element 13, individual mechanical impulses, an impulse succession or a mechanical oscillation can be transmitted to a component area of the cell membrane. As a result, an approximately circular disk-shaped area of the cell membrane is cut out of the membrane formation of the cell 3. The interior of the cell 3 can subsequently be manipulated through the opening thereby arising in the cell membrane.

Figure 7:
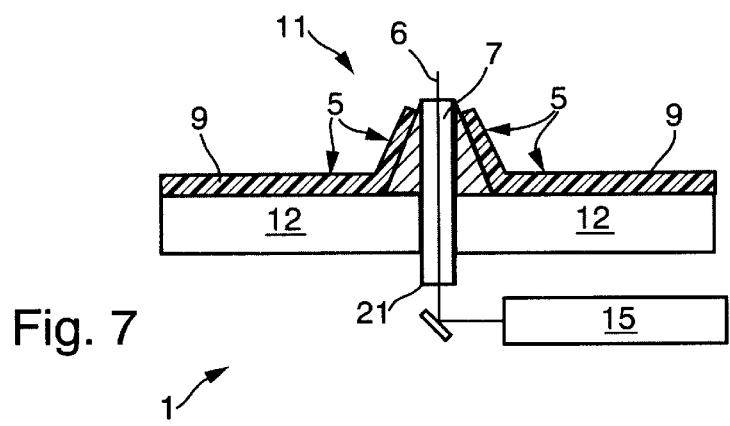
FIG. 7 is a longitudinal section through an apparatus in which a laser beam is launched into the entry channel.

In the embodiment according to FIG. 7, the poration tool 6 is a laser beam which is launchable through the entry channel 7 into the support area 5. The laser beam can be generated with an external laser 15 or by means of a laser diode incorporated into the object carrier 4. As is schematically recognizable from FIG. 7, the laser beam is launched at a site spaced from the mouth of the entry channel 7, by means of suitable radiation formation and/or guidance facilities, in the direction of extension of the entry channel 7 and exits from the support area 5 at the mouth of the entry channel 7 approximately in a direction normal to the surface of the plane stretching across the support area 5. With the laser beam a portion of the cell membrane of the biological cell deposited on the support area 5 can be irradiated. The wave length of the laser beam is selected so that the cell membrane absorbs the laser radiation. While the cell membrane is being irradiated with the laser beam, the membrane is so strongly heated that the cell membrane opens at the irradiated site. After creating the opening, the laser irradiation is turned off, so that the cell interior can then be manipulated through the opening. The insulator 9 surrounding the mouth of the entry channel 7 in the support area 5 seals the interior of the opened cell adhering to the support area 5 against the culture medium 2.

Figure 8:
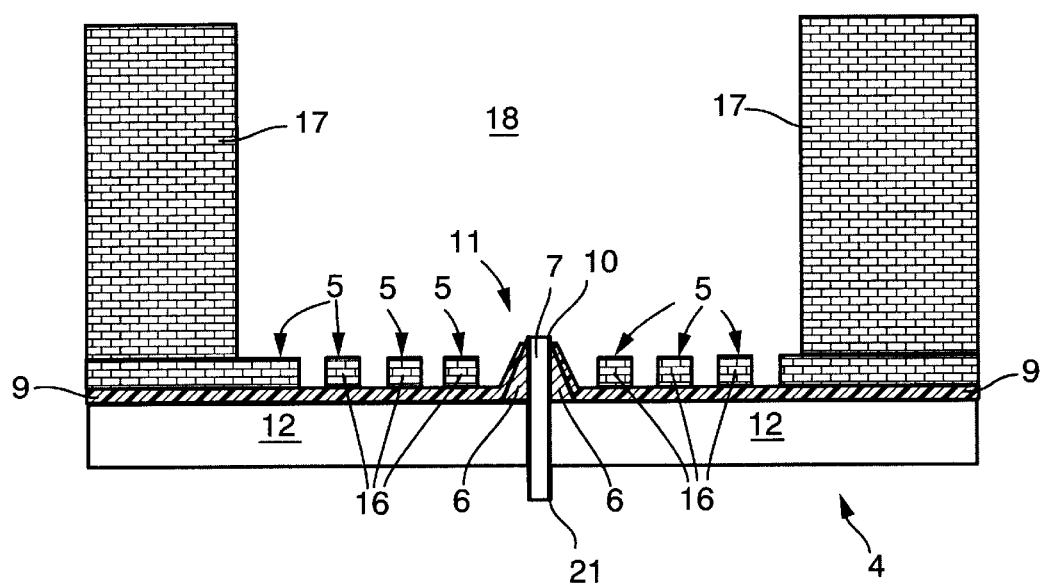
FIG. 8 is a longitudinal section through an object carrier which has a poration tool arranged between two boundary walls inside a surface structuring.

In the embodiment according to FIG. 8, a chemical substance is immobilized around the free end of the poration tool 6 having the sharp edge 10 which protrudes in relation to the surface plane of the support area 5 in an approximately annular region. Upon contact with a cell 3 deposited on the support area 5, the chemical substance creates an opening in the cell membrane. This embodiment has an especially simple construction.

Figure 4:
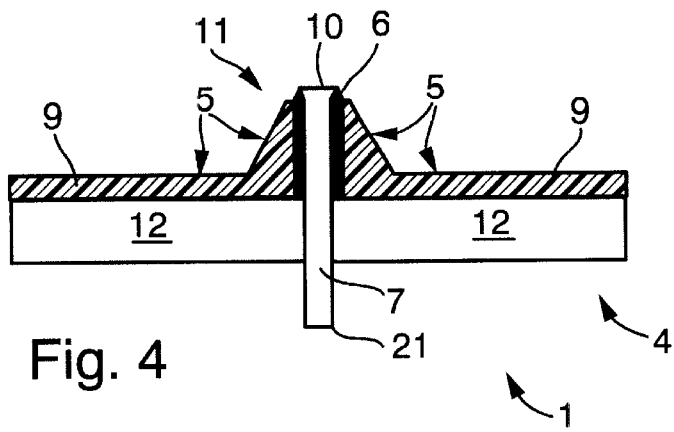
FIG. 4 is a representation similar to FIG. 2 wherein, however, the poration tool is constructed as an electrode having a substantially cylindrical shape.
Figure 5:
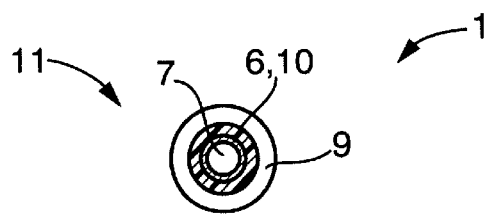
FIG. 5 is a plan view of the electrode in accordance with FIG. 4.

In the embodiment in accordance with FIGS. 4 and 5, the entry channel 7 is filled with a fluid. The entry channel 7 is connected with a pump by which the fluid contained in the entry channel 7 can be impinged with a controllable overpressure against a cell membrane of a cell 3 which is located there and seals off the opening of the entry channel 7. The edge surrounding the mouth of the entry channel 7 has an annular sharp knife edge 10 which protrudes in relation to the surface plane of the support area 5. After depositing the cell 3 on the poration tool 6, a portion of the cell membrane of the cell 3 is impinged by suction of culture medium 2 from the entry channel 7 for a short time, so strongly with underpressure that the membrane area of the cell membrane surrounded by the sharp edge 10 of the poration tool 6 is released from the membrane formation. In this manner, an opening is created in the cell membrane, through which the interior of the cell 3 can be manipulated. After creating the opening, the underpressure in the entry channel 7 is shut off.

After introducing the opening into the cell membrane of the cell 3, the pump connected with the entry channel 7 can be reversed for a short time in the direction of conveyance, in order to inject a substance situated in the entry channel 7, for example a medication and/or a fluorescence dye, through the opening of the cell membrane directly into the cell interior. If no cell 3 is positioned on the poration tool 6, the entry channel 7 can also be used to introduce an appropriate substance into the culture medium 2.

Figure 9:
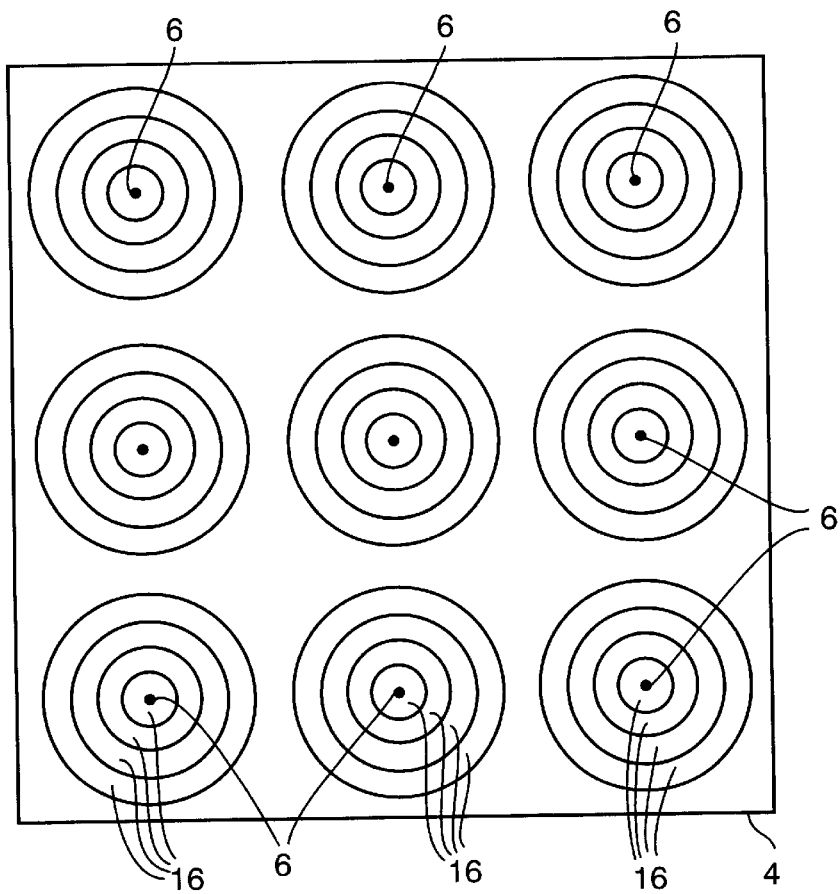
FIG. 9 is a plan view on an object carrier which has an array with a plurality of poration tools and entry channels.

In the embodiments in accordance with FIGS. 8 and 9, the object carrier 4 has several contour depressions 16 respectively running around the poration tool 6 in the support area 5. As is especially well recognizable from FIG. 1, the sealing of the cell membrane of the cell 3 against the support area 5 of the object carrier 4 is improved.

The contour depressions 16 are closed annular grooves which are arranged concentrically to the poration tool 6. The annular grooves respectively have an approximately rectangular cross section. Annular grooves adjacent to one another are respectively arranged at approximately identical distances from one another (FIG. 9). The distances of adjacent contour depressions 16 to one another and the depth of these contour depressions 16 are adapted to the type of the cells to be positioned on the support region 5. The edges of the contour depressions 16 can be rounded in order to facilitate the adherent depositing of a cell 3.

Figure 10:
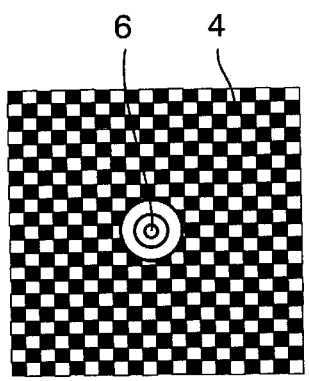
FIG. 10 is a plan view on an object carrier whose support area has a checkered structure.
Figure 11:
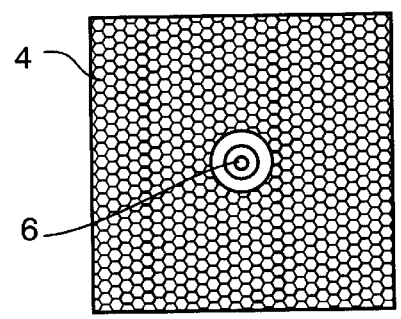
FIG. 11 is a plan view on an object carrier whose support area has a honeycomb structure.

The contour depressions 16 can have interruptions in their course, as shown with the example of a checkered structuring in FIG. 10 and a honeycomb structure in FIG. 11. The surface contours, the surface roughness and the surface material, respectively, can be adapted to a certain cell type. In this manner, cell adhesion can be improved or controlled.

In the embodiments according to FIGS. 1 and 8, the surface contour 16 is applied on the electrical insulator 9 as a coating using semiconductor technology methods. The object carrier 4 is thereby easily producible as a semiconductor chip. The surface profiling can, however, also be applied to the insulator 9 with a thick layer technique.

In the embodiment in accordance with FIG. 8, boundary walls 17 are arranged on both sides of the poration tool 6, which together with the insulator 9 form a guide channel 18 somewhat U-shaped in cross section. At the same time, the contours 16 and the poration tool 6 are arranged on the floor of the guide channel 18 between the boundary walls 17. The boundary walls 17 form an obstacle for cells 3 situated in the guide channel 18, which these cannot overcome, or cannot overcome without further effort. The cells 3 can thereby basically move essentially only in the direction of extension of the guide channel 18, whereby they necessarily come into contact with the poration tool 6.

The clear distance between the boundary walls 17 arranged on both sides of the poration tool 6 is adapted to the dimensions of the cells 3 and is preferably selected somewhat larger than the diameter of the cells 3. Optionally, several poration tools 6 can be arranged one after another in the direction of extension of the guide channel 18. In this manner, several cells 3 can be opened at the same time and manipulated intracellularly. The cross section of the guide channel 18 can taper or broaden in the direction of extension, that is, the guide channel 18 can have at different places a different width and/or different cross section dimensions. Proceeding from the deepest to the widest projecting point of the guide channel 18, the cross section of the guide channel 18 can taper, for example.

In the embodiment in accordance with FIG. 9, several poration tools 6 are arranged in the form of an array in the support area 5 of the object carrier 4. The individual poration tools 6 are respectively arranged on the grid points of a Cartesian coordinate system. The poration tools 6 can, however, also be distributed in another manner in the support area, for example in rows or columns staggered in relation to each other, or freely distributed.

Guide structures which enable a selective positioning of cells 3 can be arranged on and between the poration tools 6 for optimizing cell growth. The guide structures can, for example, include a surface structuring, a coating or an appropriate topographical configuration. For various cell types, various distances between poration tools 6 adjacent to one another can be provided.

In the embodiments depicted in the drawings, the entry channel 7 is connected respectively with a pump, by means of which culture medium 2 is sucked out of the support area 5 of the object carrier 4 and fed at another spot back to the support area 5. In this manner, the positioning of a cell 3 on the poration tool 6 is facilitated. Optionally, a weak underpressure can be exerted on the cell 3 after positioning of a cell sucked by means of the entry channel 7 onto the poration tool 6 for a certain time until the cell independently adheres to the support area 5.

In the embodiments according to FIGS. 1 to 8, the object carrier 4 is respectively constructed somewhat plate-shaped. The entry channel 7 penetrates the object carrier 4 proceeding from the support area 5 to the reverse side of the object carrier facing away from this. In the embodiment according to FIG. 1, the object carrier has a wall attenuation 20 which has a smaller wall thickness than the wall area laterally adjacent thereto. This is obtained by a funnel-shaped recess 19 arranged on the reverse side of the object carrier area having the wall attenuation 20. The cross section of the recess 19 narrows proceeding from the reverse side surface plane of the object carrier 4 to the deepest point of the recess 19. A good mechanical stability results therefrom. On the reverse side of the object carrier 4, the entry channel 7 has a connection point 21 for connection with a pump, an underpressure or over pressure reservoir, a laser or similar facility. It should still be mentioned that in the embodiments according to FIGS. 2 to 11, the object carrier can have a reduced wall thickness in the area of the entry channel 7.

It will be appreciated by those skilled in the art that changes could be made to the embodiment(s) described above without departing from the broad inventive concept thereof. It is understood, therefore, that this invention is not limited to the particular embodiment(s) disclosed, but it is intended to cover modifications within the spirit and scope of the present invention as defined by the appended claims.

We claim:

1. A process for intracellular manipulation of at least one biological cell (3) present in a culture medium and adherently deposited on a support area, comprising creating an opening in a membrane of the cell (3) and manipulating the cell interior through this opening, wherein the open is created in the cell membrane within the support area (5) for the cell (3) and at a distance from an edge of the support, and wherein the opening in the membrane of the cell is created by means selected from the group consisting of electroporation, mechanical impulse, irradiation, chemical poration and electrical, chemical or radiation activation of an activatable poration substance.

2. The process according to claim 1, wherein the opening in the cell membrane is created by means of electroporation.

3. The process according to claim 1, wherein the creating of the opening in the cell membrane comprises exerting at least one mechanical impulse on a component area of the cell membrane.

4. The process according to claim 1, wherein the creating of the opening in the cell membrane comprises irradiating a component area of the cell membrane with energy-rich radiation.

5. The process according to claim 4, wherein the energy-rich radiation comprises laser radiation.

6. The process according to claims 1, wherein the opening in the cell membrane is created by action of a chemical poration substance.

7. The process according to claim 1, wherein the creating of the opening in the cell membrane comprises providing an electrical-, chemical- or radiationact-activatable poration substance, and activating the poration substance to create the opening in the cell membrane by action of at least one of radiation, a chemical and an electrical field.

8. The process according to claim 1, wherein a portion of the cell membrane to be opened is separated from the membrane by at least one of an underpressure and an overpressure.

9. The process according to claim 1, wherein the cell (3) is fixed on the support area by a force of suction.

10. The process according to claim 1, further comprising removing or implanting at least one substance and/or cell component from/into the cell interior.

* * * * *